US012806332B2

(12) United States Patent
Yang

(10) Patent No.: US 12,806,332 B2
(45) Date of Patent: Nov. 24, 2026

(54) DRIVING APPARATUS AND DRUG INFUSION DEVICE

(71) Applicant: MEDTRUM TECHNOLOGIES INC., Shanghai (CN)

(72) Inventor: Cuijun Yang, Shanghai (CN)

(73) Assignee: MEDTRUM TECHNOLOGIES INC., Shanghai (CN)

( * ) Notice: Subject to any disclaimer, the term of this patent is extended or adjusted under 35 U.S.C. 154(b) by 791 days.

(21) Appl. No.: 17/617,308

(22) PCT Filed: Aug. 1, 2019

(86) PCT No.: PCT/CN2019/098784

§ 371 (c)(1),
(2) Date: Dec. 8, 2021

(87) PCT Pub. No.: WO2021/016975

PCT Pub. Date: Feb. 4, 2021

(65) Prior Publication Data

US 2022/0218895 A1 Jul. 14, 2022

(51) Int. Cl.
*A61M 5/142* (2006.01)
*A61B 5/145* (2006.01)
(Continued)

(52) U.S. Cl.
CPC ..... *A61M 5/14236* (2013.01); *A61B 5/14532* (2013.01); *A61M 5/14216* (2013.01);
(Continued)

(58) Field of Classification Search
CPC ........ A61M 2005/14208; A61M 5/145; A61M 2005/14533; A61M 5/14236;
(Continued)

(56) References Cited

U.S. PATENT DOCUMENTS

2004/0207385 A1* 10/2004 Gafner ...................... H02P 6/16 324/76.11
2008/0007141 A1 1/2008 Deck
(Continued)

FOREIGN PATENT DOCUMENTS

CN 102233148 11/2011
CN 106139311 11/2016
(Continued)

OTHER PUBLICATIONS

"International Search Report (Form PCT/ISA/210) of PCT/CN2019/098784," mailed on Apr. 20, 2020, pp. 1-2.
(Continued)

*Primary Examiner* — Lauren P Farrar
*Assistant Examiner* — Guillermo G Paz Estevez
(74) *Attorney, Agent, or Firm* — JCIP GLOBAL INC.

(57) ABSTRACT

A drug infusion device includes a drug storage unit, a driving unit, a position detecting area, a power unit and a control unit. The piston is disposed in the drug storage unit, and a driving rod is connected to the piston. The driving unit includes a driving part and a positioning part. The driving unit drives the driving part and the positioning part to move. The positioning part interacts with the position detecting area at different positions to trigger different position signals. The power unit applies a force to move the driving unit. The control unit is connected to the position detecting area to receive the position signals, according to the position signals, the control unit controls the direction of the force applied by the power unit to move the driving unit and form optional infusion modes.

12 Claims, 9 Drawing Sheets

(51) Int. Cl.

| | |
|---|---|
| ***A61M 5/145*** | (2006.01) |
| ***A61M 5/168*** | (2006.01) |
| ***A61M 5/315*** | (2006.01) |
| ***G16H 20/17*** | (2018.01) |
| ***G16H 40/67*** | (2018.01) |
| *A61M 5/172* | (2006.01) |

(52) U.S. Cl.

CPC ...... *A61M 5/14248* (2013.01); *A61M 5/1452* (2013.01); *A61M 5/1454* (2013.01); *A61M 5/16877* (2013.01); *A61M 5/31583* (2013.01); *G16H 20/17* (2018.01); *G16H 40/67* (2018.01); *A61M 2005/14208* (2013.01); *A61M 2005/14252* (2013.01); *A61M 2005/14506* (2013.01); *A61M 5/1723* (2013.01); *A61M 2205/0233* (2013.01); *A61M 2205/3317* (2013.01); *A61M 2205/3327* (2013.01); *A61M 2230/201* (2013.01)

(58) Field of Classification Search

CPC ........ A61M 5/14216; A61M 2205/106; A61M 2205/103; A61M 2205/3317; A61M 2205/0233; A61M 2205/0272; A61M 5/1452; A61M 2005/14506; A61M 2205/10; A61M 5/31525; A61M 5/31501; A61M 5/31545; A61M 5/31531; A61M 5/31548; A61M 5/31573; A61M 5/31538; A61M 5/31533; A61M 5/31546; A61M 5/3155; A61M 5/31568; A61M 5/31528; A61M 5/3157; G16H 20/17

See application file for complete search history.

(56) References Cited

U.S. PATENT DOCUMENTS

| | | | | |
|---|---|---|---|---|
| 2008/0188813 | A1 * | 8/2008 | Miller .................... | G01D 21/00 604/207 |
| 2013/0211370 | A1 | 8/2013 | Nzike et al. | |
| 2019/0117881 | A1 | 4/2019 | Yang | |

FOREIGN PATENT DOCUMENTS

| | | | | |
|---|---|---|---|---|
| CN | 107456625 | | 12/2017 | |
| CN | 108331731 | | 7/2018 | |
| EP | 0916353 | | 5/1999 | |
| WO | WO-2006104806 | A2 * | 10/2006 | ........ A61M 5/14546 |

OTHER PUBLICATIONS

"Search Report of Europe Counterpart Application", issued on Mar. 6, 2023, p. 1-p. 8.

* cited by examiner

DRIVING APPARATUS AND DRUG INFUSION DEVICE

CROSS-REFERENCE TO RELATED APPLICATION

This application is a 371 of international application of PCT application serial no. PCT/CN2019/098784 filed on Aug. 1, 2019. The entirety of the above mentioned patent application is hereby incorporated by reference herein and made a part of this specification.

TECHNICAL FIELD

The present invention mainly relates to the field of medical instruments, in particular to a driving apparatus and drug infusion device.

BACKGROUND

A drug infusion device can continuously deliver drug into a patient's body for disease treatment. Drug infusion devices are widely used in the field of diabetes treatment, which continuously infuse required dosage of insulin into the patient's subcutaneous tissue, thereby simulating the secretion function of the pancreas to keep the blood glucose stable. The drug fluid is usually stored inside the infusion pump. The existing drug infusion device, controlled by remote device, is usually attached directly on the patient's skin through a medical adhesive tape.

In the case of drug infusion, the infusion increment (unit infusion amount) of the existing infusion device is not adjustable, therefore the adjustment of the infusion volume and the infusion rate is limited, resulting in inflexible control and low infusion efficiency. The larger-than-required or smaller-than-required amount of drug infused into patient's body may cause substance level in the patient's body fluid to fluctuate greatly, so the purpose of more precise control of body fluid level cannot be achieved.

Therefore, there is a need in the art for a drug infusion device having an infusion mode with multiple infusion increment options and improved infusion efficiency.

BRIEF SUMMARY OF THE INVENTION

Embodiments of the present invention disclose a driving apparatus and a drug infusion device, in which the driving unit has a plurality of selectable rotation ranges, so that the drug infusion device has multiple infusion modes with different and optional infusion increments.

The invention discloses a driving apparatus, comprising: a driving unit, the driving unit includes driving part and positioning part, and the driving unit drives the driving part and the positioning part to move in different directions; position detecting area, the positioning part of the driving unit interacts with the position detecting area at different positions to trigger different position signals; a power unit connected to the driving unit, the power unit applies a force to cause the movement of the driving unit; and a control unit, the control unit is connected to the position detecting area for receiving the position signal, and the control unit is connected to the power unit, and according to the position signal, the control unit controls the direction of the force applied by the power unit, so that the driving unit can move in multiple different width ranges.

According to an aspect of the invention, the driving apparatus also comprises a driving wheel, the circumferential surface of the driving wheel is provided with gear teeth, the driving unit rotates to drive the driving part and the positioning part to move, and the driving part pushes the gear teeth to drive the driving wheel to rotate.

According to an aspect of the invention, the driving wheel comprises two sub-wheels spaced apart, the driving unit being arranged between the two sub-wheels, the driving unit comprising two driving parts, the two driving parts respectively cooperating with the two sub-wheels.

According to an aspect of the invention, the driving unit includes more than two driving parts, each driving part cooperating with a corresponding sub-wheel.

According to an aspect of the invention, the driving unit includes four driving parts, and two of the four driving parts are disposed on each side of the driving unit and cooperate with the corresponding sub-wheels.

According to an aspect of the invention, the manner in which the positioning part of the driving unit interacts with the position detecting area at different positions includes contact or non-contact.

According to an aspect of the invention, the position detecting area includes a plurality of contactors spaced apart, and the positioning part, while rotating, can be in electrical contact with the different contactors.

According to an aspect of the invention, different contactors have different potentials while the positioning part also has a fixed potential, and when the positioning part contacts one of the contactors, the potential of the contactor changes and triggers a unique position signal.

According to an aspect of the invention, the driving unit includes one positioning part.

According to an aspect of the invention, the driving unit includes two positioning parts, and the two positioning parts are each in electrical contact with different contactors to trigger different position signals.

According to an aspect of the invention, the position detecting area includes a continuous conductive area, and the positioning part is slidable on the position detecting area in the manner of continuous electrical contact.

According to an aspect of the invention, the continuous conductive area includes a connection point for connecting the control unit, and there is a contact point between the positioning part and the position detecting area; with different resistance or potential between the connection point and the contact point, different position signals can be triggered.

According to an aspect of the invention, the position detecting area includes movable conductive retaining wall, and when the positioning part contacts the conductive retaining wall to trigger the position signal, the driving unit then reaches the terminal point through one-direction rotation, and then the driving unit can start to rotate in the other direction, so that by moving the conductive retaining wall, the driving unit can be rotated in multiple different width ranges.

According to an aspect of the invention, the position detecting area includes two movable conductive retaining walls, and the driving unit moves between the two conductive retaining walls.

According to an aspect of the invention, the manner in which the positioning part interacts with the position detecting area at different positions is non-contact, and the position detecting area includes a continuous magnetic induction area or a plurality of spaced first magnetic sensing points while the positioning part is provided with the second magnetic sensing point, so the second magnetic sensing point interacts with a said first magnetic sensing point or the magnetic induction area at different positions to trigger different position signals according to the change of the magnetic field.

According to an aspect of the invention, the manner in which the positioning part interacts with the position detecting area at different positions is non-contact, and the positioning part and the position detecting area constitute different plates of a capacitor, and the positioning part rotates to different positions to cause capacitance change in order to trigger different position signals.

Correspondingly, the present invention also discloses a drug infusion device comprising: a drug storage unit; a piston disposed in the storage unit, a driving rod connected to the piston, and the driving rod can push the piston to move; driving unit, the driving unit comprises driving part and positioning part, wherein the driving part drives the driving rod to move, and the driving unit drives the driving part and the positioning part to move in different directions; position detecting area, and the positioning part interacts with the position detecting area at different positions to trigger different position signals; a power unit connected to the driving unit, the power unit applies a force to move the driving unit; and a control unit, the control unit is connected to the position detecting area to receive the position signal, and the control unit is connected to the power unit, according to the position signal, the control unit controls the direction of the force applied by the power unit to move the driving unit in multiple different width ranges to form different and optional infusion modes.

According to an aspect of the invention, the driving apparatus also comprises a driving wheel, wherein a circumferential surface of the driving wheel is provided with gear teeth, and the driving unit rotates to drive the driving part and the positioning part to rotate, the driving part pushes the gear teeth to drive the driving wheel to rotate, and the driving rod is a threaded rod in order to be driven by the driving wheel through the thread.

According to an aspect of the invention, the driving wheel comprises two sub-wheels spaced apart, the driving unit being arranged between the two sub-wheels, the driving unit comprising two driving parts, the two driving parts respectively cooperating with the two sub-wheels.

According to an aspect of the invention, the driving unit includes more than two driving parts, each driving part cooperating with a corresponding sub-wheel.

According to an aspect of the invention, the driving unit includes four driving parts, and two of the four driving parts are disposed on each side of the driving unit and cooperate with the corresponding sub-wheels.

According to an aspect of the invention, the manner in which the positioning part of the driving unit interacts with the position detecting area at different positions includes contact or non-contact.

According to an aspect of the invention, the position detecting area includes a plurality of contactors spaced apart, and the positioning part, while rotating, can be in electrical contact with the different contactors.

According to an aspect of the invention, different contactors have different potentials while the positioning part also has a fixed potential, and when the positioning part contacts one of the contactors, the potential of the contactor changes and triggers a unique position signal.

According to an aspect of the invention, the driving unit includes one positioning part.

According to an aspect of the invention, the driving unit includes two positioning parts, and the two positioning parts are each in electrical contact with different contactors to trigger different position signals.

According to an aspect of the invention, the position detecting area includes a continuous conductive area, and the positioning part is slidable on the position detecting area in the manner of continuous electrical contact.

According to an aspect of the invention, the continuous conductive area includes a connection point for connecting the control unit, and there is a contact point between the positioning part and the position detecting area; with different resistance or potential between the connection point and the contact point, different position signals can be triggered.

According to an aspect of the invention, the position detecting area includes movable conductive retaining wall, and when the positioning part contacts the conductive retaining wall to trigger the signal, the driving unit then reaches the terminal point through one-direction rotation, and then the driving unit can start to rotate in the other direction, so that by moving the conductive retaining wall, the driving unit then can be rotated in multiple different width ranges.

According to an aspect of the invention, the position detecting area includes two movable conductive retaining walls, and the driving unit moves between the two conductive retaining walls.

According to an aspect of the invention, the manner in which the positioning part interacts with the position detecting area at different positions is non-contact, and the position detecting area includes a continuous magnetic induction area or a plurality of spaced first magnetic sensing points while the positioning part is provided with the second magnetic sensing point, so the second magnetic sensing point interacts with a first magnetic sensing point or the magnetic induction area at different positions to trigger different position signals according to the change of the magnetic field.

According to an aspect of the invention, the manner in which the positioning part interacts with the position detecting area at different positions is non-contact, and the positioning part and the position detecting area constitute different plates of a capacitor, and the positioning part rotates to different positions to cause capacitance change in order to trigger different position signals.

Compared with prior arts, the technical solution of the present invention has the following advantages:

The driving apparatus disclosed by the invention comprises position detecting area and driving unit which includes a positioning part, and the positioning part interacts with the position detecting area at different positions to trigger different position signals. Different position signals can be used to determine the rotation terminal point of the driving unit, so that the driving unit can stop rotating at a plurality of optional positions, which improves the driving flexibility. In addition, according to the position signal, the control unit controls the direction of the force generated by the power unit to move the driving unit in a plurality of different width ranges. The driving unit can move in different ranges of width, so that the driven structure has various optional motion modes to improve driving efficiency.

Furthermore, the driving apparatus further includes a driving wheel. The circumferential surface of the driving wheel is provided with gear teeth. The driving unit rotates to drive the driving part and the positioning part to rotate, and the driving part pushes the gear teeth to drive the driving wheel to rotate. The driving method of the driving part pushing the teeth makes it easier to control the driving process. And through the design of the tooth pitch, each driving distance can be precisely controlled, which can further improve the controllability and stability of the driving process.

Furthermore, the manner in which the positioning part interacts with the position detecting area at different positions includes contact or non-contact. Non-contact methods such as magnetic induction and capacitance, or electrical contact method can detect the position of the positioning part sensitively and accurately. At the same time, the generated signal can be easily transmitted to the control unit.

Furthermore, the position detecting area of the driving apparatus includes movable conductive retaining wall. When the positioning part contacts the conductive retaining wall and triggers the signal, the driving unit rotates in one direction to reach the terminal point, and then the driving unit can start to rotate in the other direction. With the conductive retaining wall at different positions, the driving unit can rotate in a plurality of different width ranges. The conductive retaining wall can not only trigger the electrical signal, but also block the rotation of the driving unit, so that the driving unit reaches the terminal point of rotation, which reduces the complexity of the structural design. At the same time, the position of the moving conductive retaining wall can change the rotation range of the driving unit, improving the driving flexibility.

Correspondingly, the present invention also discloses a drug infusion device comprising position detecting area and driving unit provided with positioning part, the positioning part interacting with the position detecting area at different positions to trigger different position signals. The different position signals can be used to determine different terminal points of rotation of the driving unit, so that the infusion device has a variety of infusion pause options, which improves the flexibility of the infusion. In addition, the control unit is connected to the position detecting area to receive the position signal, and the control unit is connected with the power unit. According to the position signal, the control unit controls the direction of the force applied by the power unit, so that the driving unit can move in a plurality of different width ranges, forming different drug infusion modes. The drug infusion device has a plurality of infusion modes with different and optional infusion increments, and the patient can select different infusion modes during the infusion of the drug to strictly and accurately control the infusion of the drug, thus precisely controlling the body fluid level and improve the safety of the infusion Furthermore, the manner in which the positioning part interacts with the position detecting area at different positions includes contact or non-contact. Non-contact methods such as magnetic induction and capacitance, or electrical contact manner can detect the position of the positioning part sensitively and accurately. At the same time, the generated signal can be easily transmitted to the control unit.

Furthermore, the position detecting area of the drug infusion device includes movable conductive retaining wall. When the positioning part contacts the conductive retaining wall and triggers the signal, the driving unit rotates in one direction to reach the terminal point, and then the driving unit can start to rotate in the other direction. With the conductive retaining wall at different positions, the driving unit can rotate in a plurality of different width ranges. The conductive retaining wall can not only trigger the electrical signal, but also block the rotation of the driving unit, so that the driving unit reaches the terminal point of rotation, which reduces the complexity of the structural design. At the same time, the position of the moving conductive retaining wall can change the rotation range of the driving unit, so that the infusion device has different infusion modes, which improves the flexibility of the infusion process.

DETAILED DESCRIPTION

Figure 1:
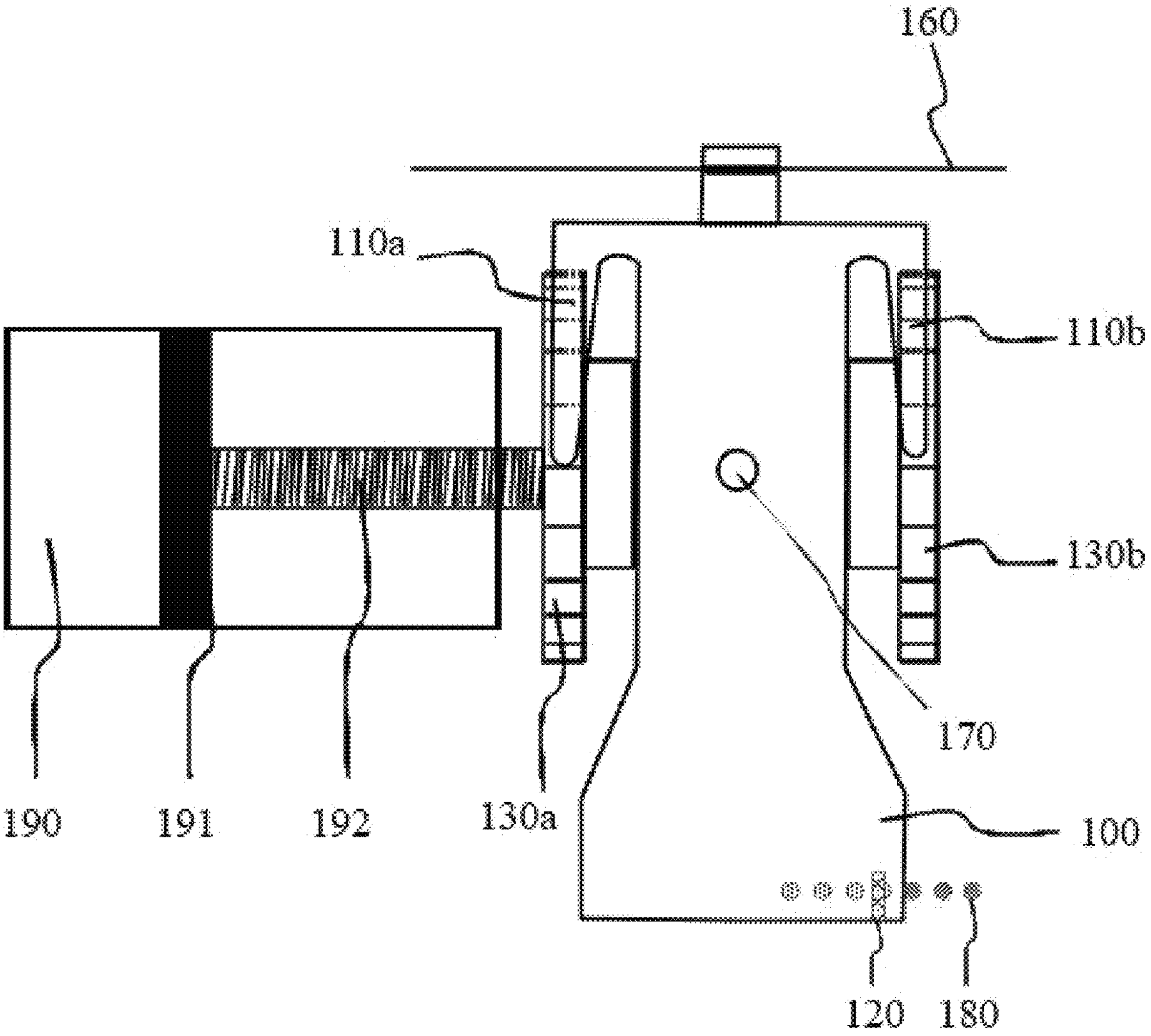
FIG. 1 is a top plan view showing a drug infusion device according to an embodiment of the present invention.

As described above, the infusion mode of the prior art drug infusion device is single, and the infusion process cannot be flexibly controlled, leading to low infusion efficiency.

It has been found through research that the cause of the above problem is that there is only one motion type and mode of the internal driving unit in the device. Under the control of the control unit, the drug infusion process cannot be manually adjusted.

In order to solve this problem, the present invention provides a drug infusion device with a plurality of optional rotation ranges in the device such that the drug infusion device has a number of optional infusion modes, increasing the controllability of the infusion process, and also the amount of drug infused will be more accurate.

Various exemplary embodiments of the present invention will now be described in detail with reference to the drawings. The relative arrangement of the components and the steps, numerical expressions and numerical values set forth in the embodiments are not to be construed as limiting the scope of the invention.

In addition, it should be understood that, for ease of description, the dimensions of the various components shown in the figures are not necessarily drawn in the actual scale relationship, for example, the thickness, width, length or distance of certain units may be exaggerated relative to other structures.

The following description of the exemplary embodiments is merely illustrative, and is not intended to be in any way limiting the invention and its application or use. The techniques, methods and devices that are known to those of ordinary skill in the art may not be discussed in detail, but such techniques, methods and devices should be considered as part of the specification.

It should be noted that similar reference numerals and letters indicate similar items in the following figures. Therefore, once an item is defined or illustrated in a drawing, it will not be discussed further in following description of the drawings.

FIG. 1 is a schematic top view of a drug infusion device according to an embodiment of the present invention.

The drug infusion device of the embodiment of the present invention includes a drug storage unit 190, a piston 191, and a driving rod 192 connected to the piston 191, and a driving unit 100. The moving driving unit 100 pushes the driving rod 192, thereby causing the driving rod 192 to advance the piston 191 to complete the drug infusion process.

The driving unit 100 includes driving part 110 and positioning part 120. The driving unit 100, through movement, drives the driving part 110 and the positioning part 120 to complete the driving process.

It should be noted that the movement modes of the driving unit 100 includes rotation, swing (linear or non-linear), and the like. Specifically, in the embodiment of the present invention, the driving unit 100 moves in a rotating manner. Therefore, in the embodiment of the present invention, the drug infusion device further includes a rotating shaft 170.

It should be noted that the position of the rotating shaft 170 is not particularly limited as long as the embodiment of the present invention can satisfy the condition for rotating the driving unit 100. As in some embodiments of the present invention, the rotating shaft 170 is disposed at one end of the driving unit 100 or at a certain part in the middle, and the purpose can be achieved in each case.

The embodiment of the present invention also does not limit the positional relationship between the positioning part 120 and the driving part 110. As in one embodiment of the present invention, the positioning part 120 is disposed near the non-driving end of the driving part 110, which can also realize the purpose of detecting the position.

The drug infusion device of the embodiment of the present invention further includes a position detecting area 180, a power unit 160 and a control unit (not shown).

When the driving unit 100 rotates to different positions, the positioning part 120 interacts with the position detecting area 180 to trigger different position signals. In an embodiment of the invention, the manner in which the two interact with other includes contact or non-contact. Therefore, the triggered position signal includes contact signal or non-contact signal.

The power unit 160 is used to apply a force to the driving unit 100 to move the driving unit 100. The power unit 160 is connected to the control unit, and under the control of the control unit, the power unit 160 adjusts the magnitude and direction of the force applied to the driving unit 100 continuously to adjust the speed and movement range of the driving unit 100.

The control unit is connected to the position detecting area 180 to receive the generated position signal, thereby controlling and adjusting the force applied by the power unit 160. At the same time, the control unit of the embodiment of the invention is also capable of remotely receiving and transmitting infusion signals to meet different infusion requirements, thereby completing the infusion process. Or the control unit can automatically control the drug infusion process according to the received body fluid signal, without manual intervention.

In an embodiment of the invention, the drug infusion device further includes a driving wheel 130. The circumferential surface of the driving wheel 130 is provided with gear teeth (not shown in FIG. 1), and the driving unit 100 rotates and drives the driving part 110 to push the gear teeth, thereby pushing the driving wheel 130 to rotate. In the embodiment of the invention, the teeth are ratchet teeth, which facilitate pushing in only one direction.

In an embodiment of the invention, the driving wheel 130 is coupled to the driving rod 192 and the driving rod 192 is a threaded rod. When the driving wheel 130 rotates, the driving rod 192 is pushed forward by the thread to complete the drug infusion.

It should be noted that, in other embodiments of the present invention, the drug infusion device may not include the driving wheel 130, and the driving part 110 drives the driving rod 192 through other driving conversion units, and the drug infusion process can also be completed.

In the embodiment of the present invention, the driving wheel includes two sub-wheels 130*a* and 130*b* spaced apart. The driving unit 100 includes two driving parts 110*a* and 110*b*, and the two driving parts 110 respectively cooperate with the two sub-wheels. The driving unit 100 is disposed between the two sub-wheels. The driving unit 100 rotates around the rotating shaft 170 to drive the driving part 110 to alternately push the sub-wheels to rotate.

Figure 2A:
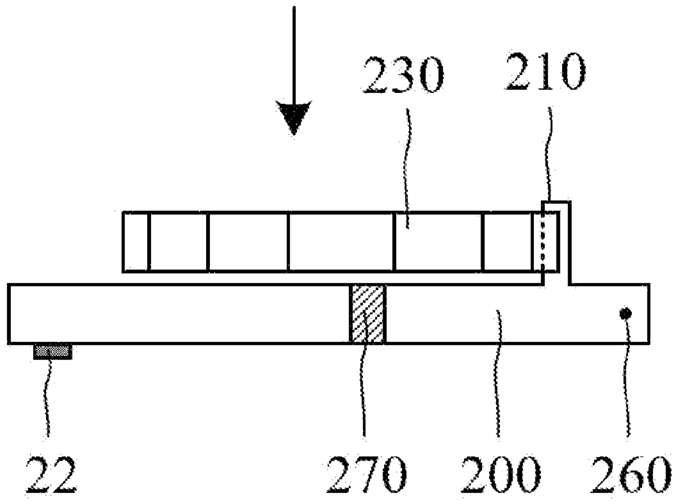
FIG. 2*a* to FIG. 2*b* are schematic structural views of a driving unit having a driving part and a positioning part according to an embodiment of the present invention.
Figure 2B:
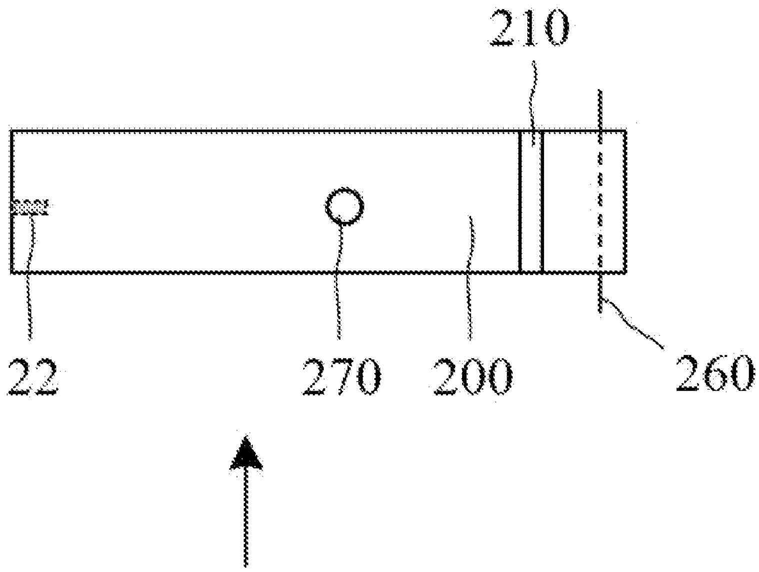

FIG. 2*a* and FIG. 2*b* are schematic diagrams showing the structure of a driving unit 200 including only one driving part 210 according to an embodiment of the present invention. FIG. 2*a* is a schematic view of the structure as viewed in the direction of the arrow of FIG. 2*b*, and FIG. 2*b* is a schematic view of the structure as seen by the direction of the arrow in FIG. 2*a*.

The rotating shaft 270 is disposed on a base (not shown), and the power unit 260 pulls the driving unit 200 to rotate around the rotating shaft 270 to drive the driving part 210 and the positioning part 22 to move. Since the driving unit 200 has only one driving part 210, in the embodiment of the present invention, only one driving wheel 230 is engaged with the driving part 210. And the driving part 210, an elastic member, can not only push the teeth when rotating in one direction, but also slide on the teeth while rotating in the opposite direction. In order to show the structure of the driving unit 200 clearly, the driving wheels are not shown in FIG. 2*b*.

Figure 3:
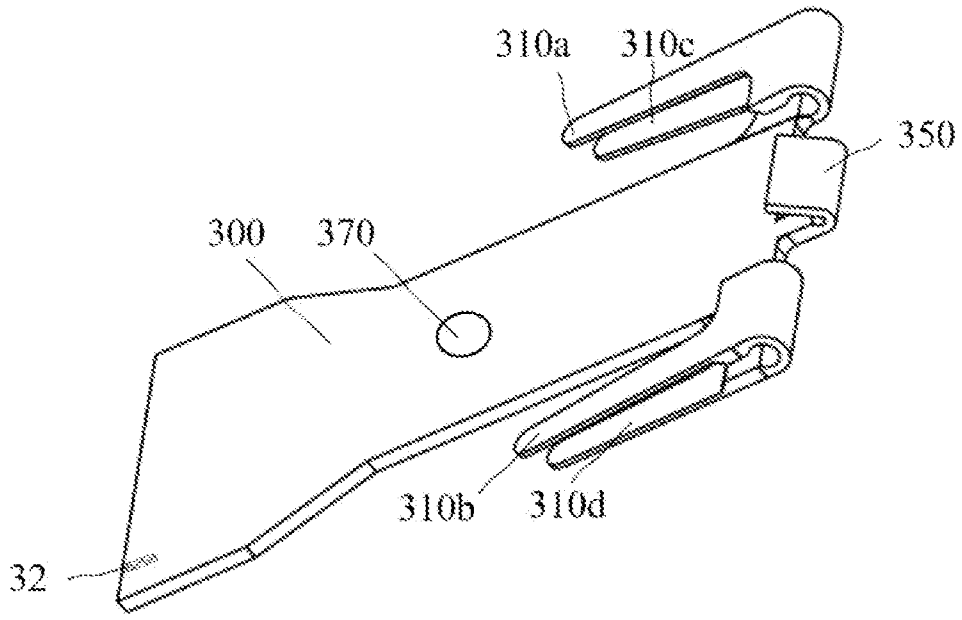
FIG. 3 is a schematic structural view of a driving unit including four driving parts according to an embodiment of the present invention.

FIG. 3 is a schematic structural diagram of a driving unit 300 including four driving parts 310 according to an embodiment of the present invention.

The drug infusion device of the embodiment of the present invention does not limit the number of driving parts, and there may be one or two, as described above. Further, there may be three, four or more than four driving parts. When there are two or more driving parts, the driving wheel includes two sub-wheels, as shown in FIG. 1, thus different driving parts respectively cooperate with corresponding sub-wheels.

As shown in FIG. 3, in one embodiment of the present invention, the driving unit 300 includes four driving parts 310*a*, 310*b*, 310*c*, and 310*d*. 310*a* and 310*c* are disposed on one side of the driving unit 300 and cooperate with one sub-wheel, while 310*b* and 310*d* are disposed on the other side of the driving unit 300 to cooperate with the other sub-wheel. Obviously, in other embodiments of the present invention, when the number of the driving parts 310 is an odd number greater than or equal to 3, the numbers of driving parts disposed on each side of the driving unit 300 are different, that is, the numbers of driving parts matched with each sub-wheel are different, but the driving requirements of the present invention can still be satisfied.

It should be noted that, in the embodiment of the present invention, the tooth pitch of the gear can be set according to the situation, and when the driving part of one side pushes the gear teeth, the driving part of the other side slides on the surface of the gear tooth, The sliding distance can be less than, or equal to, or greater than one pitch. When the driving unit rotates in the other direction, the position of the previously sliding driving part is adjusted after a period of time, and the gear teeth can also be driven to drive the driving wheel to move, which is not specifically limited.

Embodiments in which the driving unit includes two driving parts will be described in detail below.

Figure 4A:
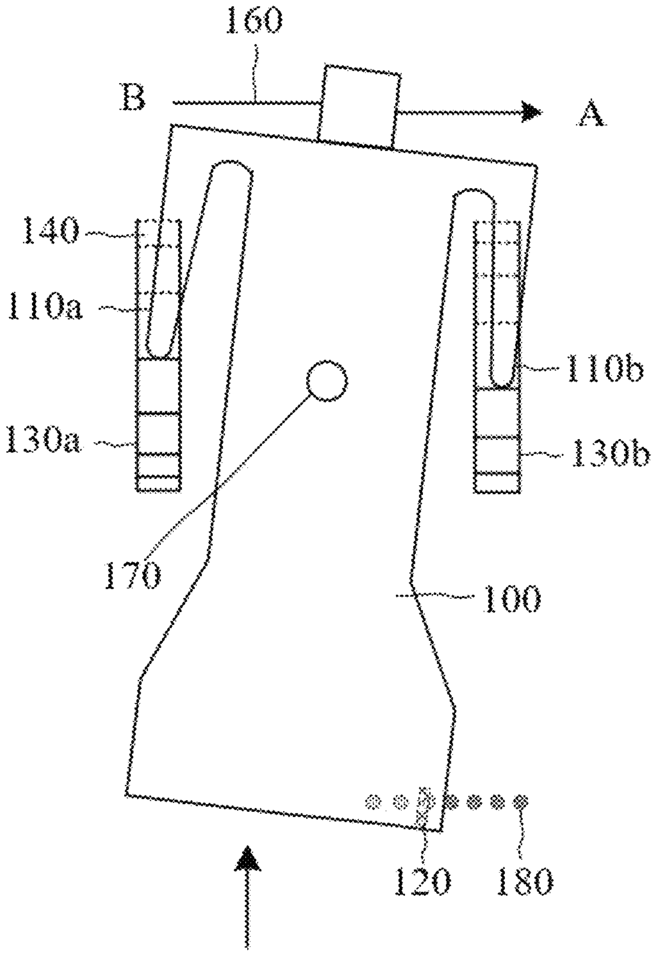
FIG. 4*a* to FIG. 4*c* are schematic structural views of a position detecting area including a plurality of contactors spaced apart according to another embodiment of the present invention.
Figure 4B:
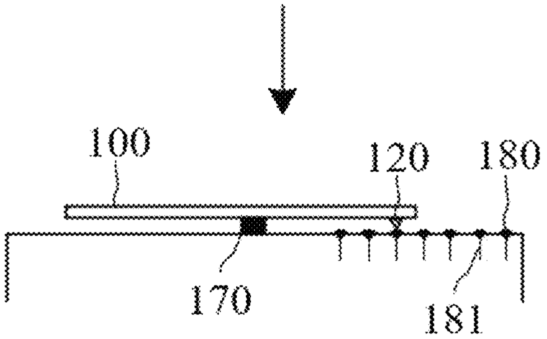
Figure 4C:
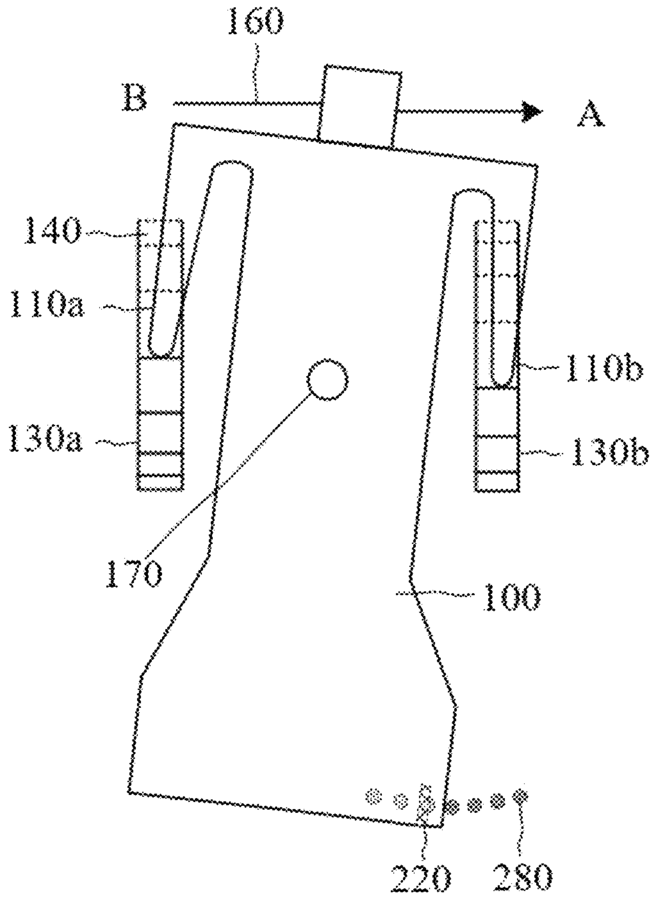

FIG. 4*a* to FIG. 4*c* are respectively two top plan views and a side view of the position detecting area 180 and the positioning unit 120 according to an embodiment of the present invention. FIG. 4*a* is a schematic top view of the structure taken along the direction of the arrow of FIG. 4*b* (when the similar viewing angles of the structural diagrams in other embodiments are the same as here, it will not be described below).

As shown in FIG. 4*a* to FIG. 4*c*, in an embodiment of the invention, position detecting area 180 includes a plurality of contactors spaced apart. The contactors are in the shape of a spherical cap and are arranged in a straight line at intervals. As shown in FIG. 4*c*, in another embodiment of the invention, the contactor spacing arrangement is in the form of an arc.

It should be noted that, in other embodiments of the present invention, the shape and arrangement of the contactors may also include other types, which are not specifically limited herein, as long as the conditions for generating the position signals can be satisfied.

In the embodiment shown in FIG. 4*a* to FIG. 4*c*, there is only one positioning part 120 and one position detecting area 180, and the positioning part 120 and the position detecting area 180 are disposed on the same side of the driving unit 100. In other embodiments of the present invention, the positioning part 120 and the position detecting area 180 may be disposed at other positions as long as they can cooperate with each other to satisfy the conditions for detecting position and triggering position signal, and are not specifically limited herein.

FIG. 4*b* is a schematic side view of the structure taken along the direction of the arrow of FIG. 4*a* (when the similar viewing angles of the structural diagrams in other embodiments are the same as here, it will not be described below). When the driving unit 100 is rotated to different positions, the positioning part 120 is in electrical contact with different contactors, and different position signals can be triggered. Specifically, in the embodiment of the present invention, the potentials of the different contactors are different, and the positioning part 120 also has a fixed potential (the potential may be a negative value, 0 or a positive value). Therefore, when the positioning part 120 is in contact with different contactors, the potential of the contactor changes, or the potential difference measured at different positions changes, and the electric signal generated by the change of the potential (or the potential difference) which serves as position signal is transmitted to the control unit through the wire 181. The control unit determines whether the driving unit 100 has reached the end of rotation in the selected infusion mode (including the infusion mode and/or the infusion rate mode). If the required infusion mode is not met, that is, the driving unit 100 has not reached the end of rotation in that direction, the control unit continues to instruct the power unit 160 to pull the driving unit 100, leading driving unit 100 to continue rotating in that direction until the end of the rotation is reached. And then it can rotate in the other direction.

Obviously, when the desired amount of drug has been infused, the driving unit 100 will stop rotating once it has reached the terminal point and drug infusion will be suspended until the driving unit 100 performs the next infusion instruction.

Specifically, in one embodiment of the invention, the different contactors have different positive potentials and the potential of the positioning part 120 is zero (or ground, or negative). When the positioning part 120 is in contact with different contactors, the control unit can receive different potential signals representing different position signals, based on which the control unit controls the force applied by the power unit 160.

As shown in FIG. 4*a* to FIG. 4*c*, it is obvious that there are multiple contactors in the embodiment of the present invention. According to different actual infusion requirements, after receiving the instruction of the selected infusion mode, the control unit controls the power unit 160 to ensure that the driving unit 100 stops rotating after contacting a specific contactor, and then starts to rotate in the other direction. By analogy, the driving unit 100 can complete the rotation cycle within a certain width range, thereby completing the infusion process of the selected infusion mode. Therefore, in the embodiment of the present invention, the driving unit 100 rotates in a number of different width ranges, thereby pushing the driving rod and the piston to move different lengths in order to adjust the drug infusion amount and drug infusion rates.

As shown in FIG. 4*b*, the contactors of the position detecting area 180 are protruding from the surface of the base (not shown) to ensure sufficient contact with the positioning part 120. Each contactor is connected to the control unit via a wire 181 through which an electrical signal can be passed.

FIG. 4*c* is a schematic structural view of a contact of a position detecting area 280 according to another embodiment of the present invention. Multiple contactors spaced apart are arranged in an arc shape, and the radian is coincident with the rotation radian of the positioning part 220. Its side view is identical to FIG. 4*b* and will not be described again here.

Figure 5A:
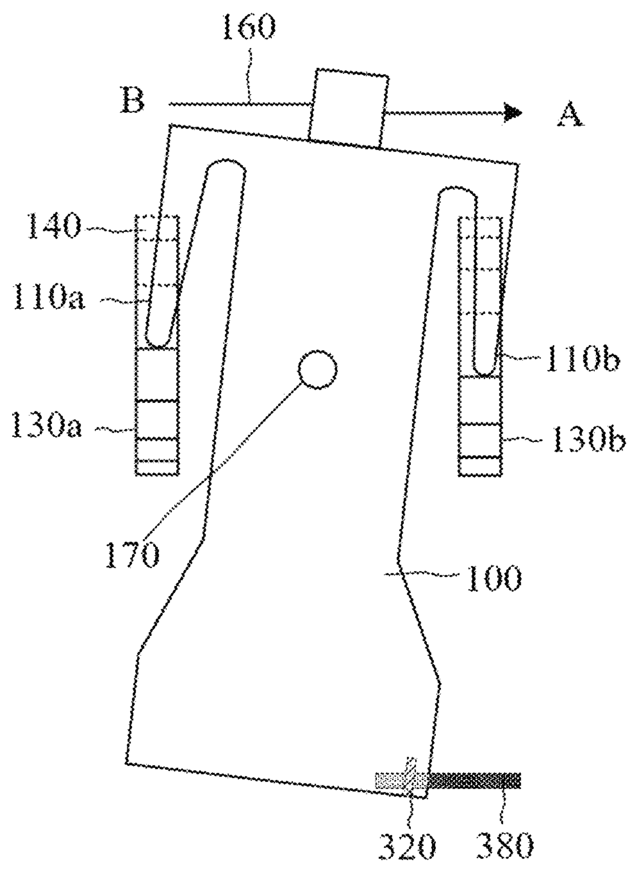
FIG. 5*a* to FIG. 5*b* are schematic structural views of a position detecting area including a continuous conductive area according to still another embodiment of the present invention.
Figure 5B:
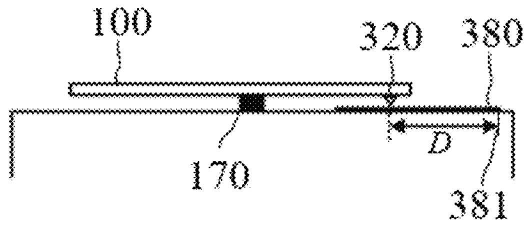

FIG. 5*a* and FIG. 5*b* are schematic diagrams showing the structure of a position detecting area 380 and a positioning part 320 according to still another embodiment of the present invention.

In the embodiment of the present invention, the position detecting area 380 includes continuous conductive area, and the positioning part 320 can incessantly contact and slide on the position detecting area 380. As described above, the position detecting area 380 and the positioning part 320 are both disposed on the same side of the driving unit 100.

As shown in FIG. 5*b*, the position detecting area 380 is protruding from the surface of the base to facilitate continuous contact with the positioning part 320.

The position detecting area 380 also includes a connection point a at which the wire 381 is connected to the control unit. The position where the positioning part 320 and the position detecting area 380 are in sliding contact is the contact point b. Since the positioning part 320 continuously contacts and slides on the position detecting area 380, the position of the contact point b changes with the rotation of the driving unit 100, and the length of the range D between the connection point a and the contact point b changes. Therefore, the position signal of the driving unit 100 is determined and triggered by measuring the resistance or potential within a certain range D between the connection point a and the contact point b. During the rotation of the driving unit 100, the width and the range between the contact point b and the connection point a are changing, and the measured resistance or potential is also changing. Different resistance values or potential values correspond to different positions, therefore unique position information can be sent to the control unit through electrical signal. Therefore, the driving unit 100 of the embodiment of the present invention can be rotated within a plurality of different widths ranges under the control of the control unit, so that the drug infusion device has a plurality of different and optional infusion modes.

It should be noted that other embodiments of the present invention do not specifically limit the position and the number of the connection point a, and the number of position detecting area 380 and the positioning part 320 may each be set to be two or more. Through the design of a circuit corresponding with the number of connection points a, much more precise positioning can be achieved.

In some other embodiments of the present invention, the position detecting area is a continuous slide rail on which the positioning part can continuously contact and slide. Or a groove is disposed in the position detecting area, and the positioning part cooperates with the groove to continuously contact and slide in the groove to trigger the position signal, which is not specifically limited herein.

Figure 6A:
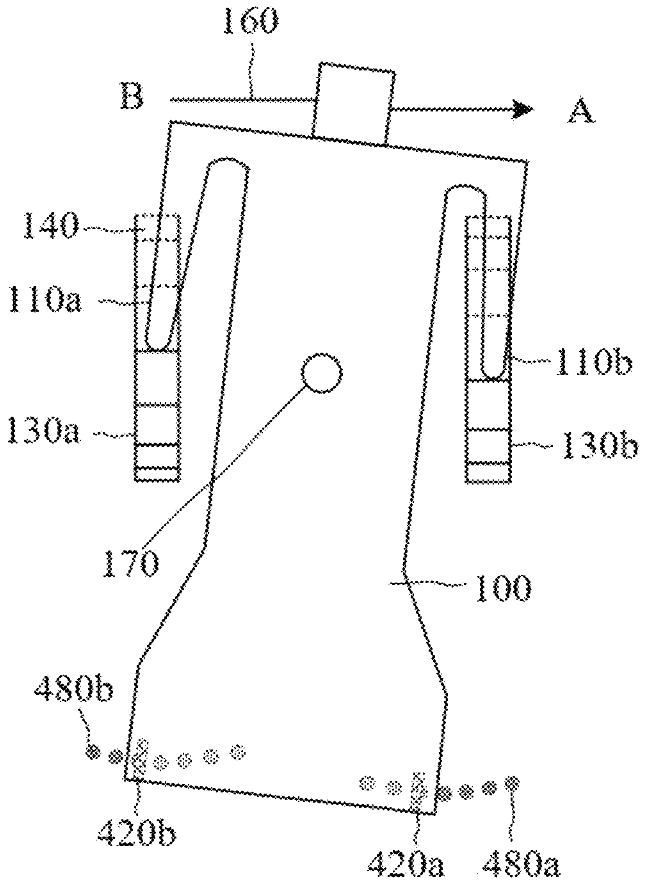
FIG. 6*a* to FIG. 6*b* are schematic structural views including two position detecting areas according to still another embodiment of the present invention.
Figure 6B:
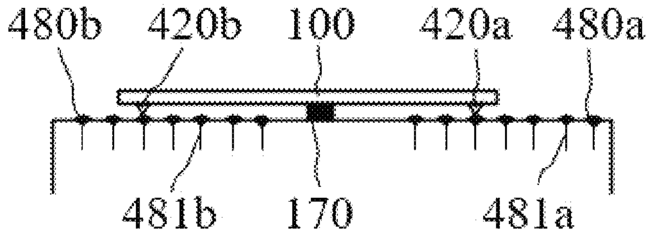

FIG. 6*a* to FIG. 6*b* are schematic diagrams showing the structure of two positioning parts and two position detecting areas according to an embodiment of the present invention.

The drug infusion device of the embodiment of the present invention includes two positioning parts 420*a* and 420*b*, and two position detecting areas 480*a* and 480*b* which both include a plurality of spaced apart contactors. The position detecting area 480*a* cooperates with the positioning part 420*a*, and the position detecting area 480*b* cooperates with the positioning part 420*b*, and they are respectively disposed on each side of the driving unit 100. The manners and working principles of the position detecting area 480*a* and the positioning part 420*a*, or the position detecting area 480*b* and the positioning part 420*b* are respectively matched with the foregoing, and are not described herein again.

As shown in FIG. 6*b*, likewise, each of the contact lead wires 481*a* or 481*b* is connected to the control unit. The positioning parts 420*a* and 420*b* can be respectively in contact with different contactors to trigger different position signals. In one embodiment of the invention, the positioning parts 420*a* and 420*b* can be in contact with different contactors at the same time, and the control unit can receive two position signals simultaneously, which can achieve more precise positioning. In another embodiment of the present invention, during the rotation of the positioning parts 420*a* and 420*b*, only one positioning part may be in contact with the contactors to trigger a position signal without the two positioning parts simultaneously contacting different contactors, and no specific limitation is made here.

It should be noted that, in other embodiments of the present invention, the position detecting area 480*a* on one side may be a continuous conductive area, and the position detecting area 480*b* on the other side may be a plurality of contactors spaced apart, or both of the position detecting areas 480*a* and 480*b* may be continuous conductive areas. No specific restrictions are made here.

Moreover, in one embodiment of the present invention, the positioning part includes two parts 420*a* and 420*b*, and there is only one position detecting area. Similarly, the position detecting area includes a plurality of contactors spaced apart or continuous conductive areas. In this case, the range of the position detecting area is wide, and spans from one side of the driving unit 100 to the other side, and can be in contact with the two positioning parts 420*a* and 420*b*, respectively.

Figure 7A:
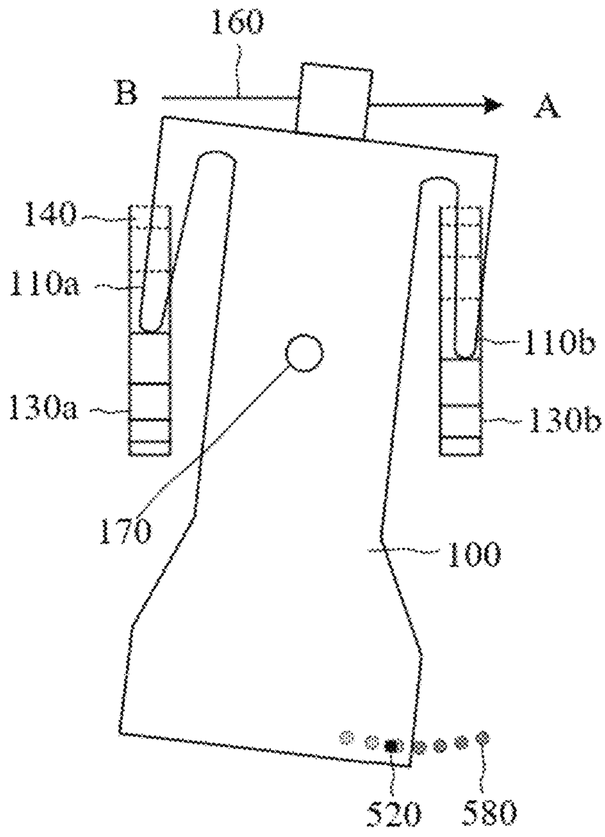
FIG. 7*a* to FIG. 7*b* are schematic diagrams showing the structure of a position detecting area for triggering a magnetic signal according to still another embodiment of the present invention.
Figure 7B:
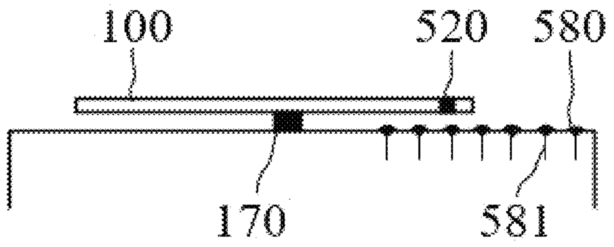

FIG. 7*a* to FIG. 7*b* are schematic diagrams showing the structure of a position detecting area 580 and a positioning part 520 for triggering a magnetic signal according to an embodiment of the present invention.

The manner of interaction between the position detecting area 580 and the positioning part 520 also includes a non-contact type.

As in the embodiment of the present invention, the position detecting area 580 includes a plurality of first magnetic sensing points spaced apart, and the positioning part 520 includes a second magnetic sensing point. When the driving unit 100 rotates to different positions, the second magnetic sensing point interacts with different first magnetic sensing points to cause a change in the strength and direction of the magnetic field. At different positions, the strength and direction of the magnetic field will be different, thus triggering different magnetic signals. The magnetic signal is transmitted to the control unit through the connecting line 581, serving as a position signal of the driving unit 100.

Similarly, in other embodiments of the invention, the position detecting area may further comprise a continuous magnetic induction area, or as previously described, the drug infusion device comprises two position detecting areas 580 and two positioning parts 520. The two position detecting areas 580 may include a plurality of first magnetic sensing points spaced apart, or include continuous magnetic induction areas at the same time. Or one of the position detecting areas 580 may include magnetic sensing points spaced apart, while the other position detecting area being a continuous magnetic induction area. Or in the infusion device, a wide range of position detecting area 580 and two positioning parts 520 are included, and are not specifically limited herein as long as it can trigger magnetic position signals.

The principle and manner of controlling the rotation of the driving unit 100 according to the triggered magnetic signal are consistent with those described above, and are not described herein again. Different from the previous method of triggering electrical signals, the second magnetic sensing point and the first magnetic sensing point or the continuous magnetic induction area can trigger different magnetic position signals without direct contact. In order not to affect the motion of the driving unit 100, the magnetic field strength of the first magnetic sensing point, the second magnetic sensing point or the continuous magnetic induction area may be small as long as the purpose of generating magnetic signals can be achieved.

In another embodiment of the present invention, the positioning part and the position detecting area are different plates of the capacitor with a certain distance between them. When the position of the positioning part changes, the capacitor plate area can change, thus causing changes in capacitance and triggering different position signals.

It should be noted that, in other embodiments of the present invention, other non-contact methods for triggering position signals are also included, such as the way of mutual inductance, which is not specifically limited herein, as long as the target measurement value can be acquired by the position change of the positioning part.

In the embodiment of the invention illustrated in FIG. 4*a* to FIG. 7*b*, the terminal points of rotation of the driving unit 100 are all controlled by the control unit according to position signals, rather than being stopped by a fixedly configured structure block. It is just because of this above mode of control that the drug infusion device of the embodiments of the present invention has a variety of alternative infusion modes or infusion rate modes.

Figure 8:
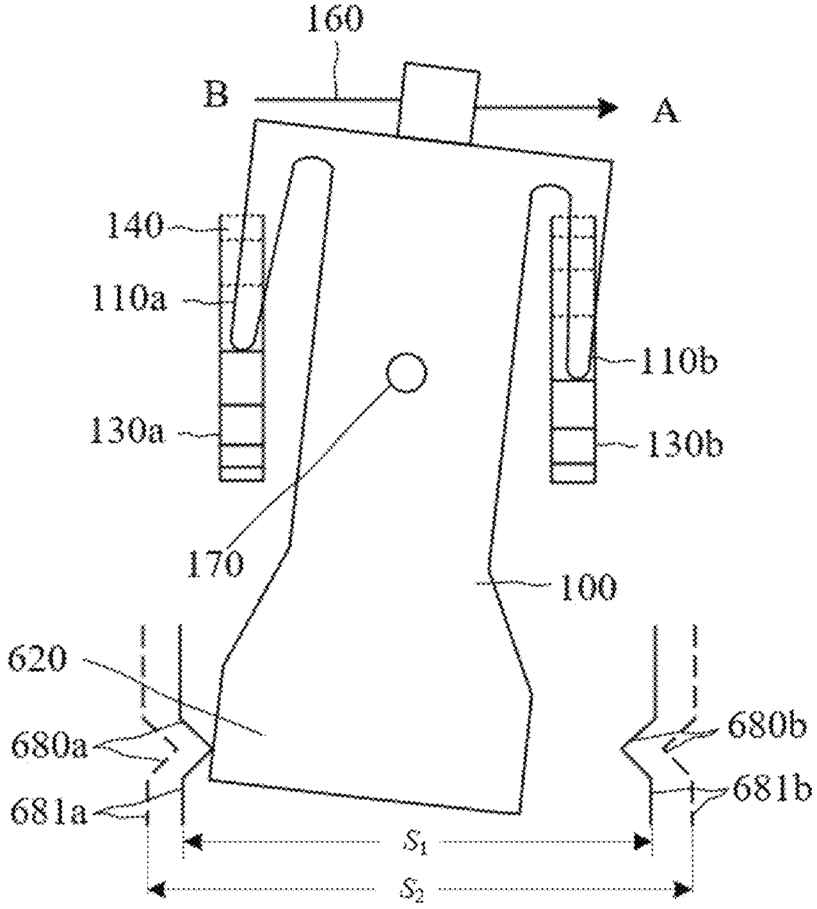
FIG. 8 is a schematic structural view of a position detecting area including two movable retaining walls according to still another embodiment of the present invention.

FIG. 8 is a block diagram showing the structure of movable position detecting area 680 according to an embodiment of the present invention.

In the embodiment of the present invention, the position detecting area 680 includes two movable conductive retaining walls 680*a* and 680*b*. In this case, the part of the driving unit 100 that can contact the conductive retaining wall is the positioning part 620. The positioning part 620 rotates between the two conductive retaining walls. The control unit is capable of controlling the movement of the conductive retaining wall. Thus, in an embodiment of the invention, the electrically conductive retaining wall 680 can simultaneously trigger a position signal and block the driving unit 100 from rotating.

After the driving unit 100 rotates, it contacts the conductive retaining wall 680*a* or 680*b* through the positioning part 620, thereby triggering the position signal. Electrical signals are transmitted to the control unit via wires 681*a* or 681*b*. When the driving unit 100 is in contact with the conductive retaining wall 680*a*, the rotation terminal point signal is triggered, and the driving unit 100 can start to rotate in the other direction. The rotation range of the driving unit 100 between the conductive retaining walls is $S_1$. When the conductive retaining walls 680*a* and/or 680*b* are moved horizontally, the range of rotation of the driving unit 100 between the conductive barriers is $S_2$, and it is obvious that the width ranges $S_1$ and $S_2$ are different. By analogy, by changing the position of the movable conductive retaining wall, the driving unit 100 can be rotated over a range of different widths, ultimately forming different and optional drug infusion modes.

Obviously, in one embodiment of the present invention, one side of the driving unit 100 is provided with one conductive retaining wall, and the other side can be disposed as a plurality of contactors spaced apart, or continuous conductive areas, or magnetic sensing points, as described above. In this case, the driving unit 100 is correspondingly provided with a positioning part that cooperates with the above contactors, areas or points. It is also possible to trigger different position signals, forming different and optional drug infusion modes.

It should be noted that, in other embodiments of the present invention, the conductive retaining wall can also be vertically moved, or the range of rotation of the driving unit 100 can be adjusted in a manner of oblique movement or three-dimensional space movement. As long as the conditions for triggering different positions signals can be satisfied, there are no specific restrictions herein.

When the driving unit in the drug infusion device rotates once in one direction, the amount of drug delivered is the unit infusion amount (or the minimum infusion amount) of the infusion device, also referred to the infusion increment of the infusion device. In a kind of infusion device, the driving unit can only rotate within a fixed range, the infusion increment cannot be changed, while only the infusion frequency can be changed, so the adjustment method is very limited. The infusion device has a relatively simple control method and only one kind of infusion increment, and the infusion process cannot be flexibly controlled.

The driving unit of the drug infusion device of the embodiment of the invention has an optional and adjustable rotation range. In different rotation ranges, the driving unit rotates once in one direction, and the amount of drugs infused by the device is different, that is, the infusion device has different infusion increments or unit infusion amounts (minimum infusion amounts). For example, when infusing insulin, the infusion increment (minimum infusion amount/unit infusion amount) can be 0.2 U, 0.15 U, 0.1 U, 0.75 U, 0.05 U, 0.025 U, 0.01 U, 0.005 U, etc. With constant frequency of rotation, the drug infusion device can have multiple infusion amount modes, or in the different infusion amount modes, the driving unit performs the same time in one rotation cycle, thus realizing the purpose different infusion rates or infusion amounts. For example, when a food bolus is required, the patient can select a larger rotation range at the beginning of the infusion, that is, to select an infusion mode with a larger infusion increment to speed up the infusion. After infusing for a period of time, select the mode in which the infusion increment is moderate. When the infusion is nearing completion, select the infusion increment to be small, resulting in slow infusion. This method splits the entire infusion process into several different sub-processes, selecting different infusion modes in different sub-processes and precisely controlling the entire infusion process. In addition, different infusion modes can be selected for basal deliveries. At the same time, the drug infusion device of the embodiment of the invention has adjustable rate of infusion (that is, the frequency of rotation of the driving unit), and patients can select from multiple different infusion rates to save infusion time and to improve infusion efficiency, which enhances users' experience.

In summary, the present invention discloses a drug infusion device. The driving unit has a plurality of different width motion ranges, so that the infusion device has different and optional infusion modes. Patients can select different infusion modes according to actual conditions. Or the infusion device automatically selects different infusion modes according to received body fluid data, thus improving the infusion efficiency, and accurately controlling the infusion process, and keeping the body fluid data level stable.

Accordingly, with continued reference to FIG. 2*a* to FIG. 8, the present invention also discloses a driving apparatus. The driving apparatus comprises a driving unit, a power unit, a control unit, and a position detecting area.

The power unit is used to apply a force to the driving unit to move the driving unit. The power unit is connected to the control unit, and under the control of the control unit, the power unit adjusts the magnitude and direction of the force applied force to the driving unit continuously to adjust the speed and movement range of the driving unit.

The driving unit includes driving part and positioning part, and the driving unit, through movement, drives the driving part and the positioning part to complete the driving process. The movement modes of the driving unit include rotation, rocking (linear or non-linear). Specifically, in an embodiment of the invention, the driving unit moves in a rotating manner. Therefore, in an embodiment of the invention, the driving unit further includes a rotating shaft.

Embodiments of the present invention also do not limit the positional relationship between the positioning part and the driving part. As in one embodiment of the present invention, the positioning part is disposed near the non-driving end of the driving part, which can also realize the purpose of detecting the position.

It should be noted that the embodiment of the present invention does not specifically limit the position for disposing the rotating shaft, as long as the condition for rotating the driving unit can be satisfied. As in some embodiments of the present invention, the rotating shaft is disposed at one end of the driving unit or at a certain part in the middle, and the purpose can be achieved.

The position detecting area is used to interact with the positioning part to trigger position signals. When the driving unit is rotated to different positions, the positioning part interacts with the position detection area to trigger different position signals. In an embodiment of the invention, the manner in which the two interact with other includes contact or non-contact. Therefore, the triggered position signal includes contact signal or non-contact signal.

The control unit is connected to the position detecting area to receive the generated position signal, thereby controlling and adjusting the force applied by the power unit.

In an embodiment of the invention, the driving apparatus further includes a driving wheel. The circumferential surface of the driving wheel is provided with gear teeth (not labeled), and the driving unit drives the driving part to push the gear teeth, thereby pushing the driving wheel to rotate. In the embodiment of the invention, the teeth are ratchet teeth, which facilitate pushing in only one direction.

In an embodiment of the invention, the driving wheel is coupled to the driving rod and the driving rod is a threaded rod. When the driving wheel rotates, the driving rod is advanced by threading.

It should be noted that, in other embodiments of the present invention, the driving apparatus may not include a driving wheel, and the driving part interacts with the driving rod through other driving conversion units.

In the embodiment of the invention, the driving wheel comprises two sub-wheels spaced apart, and the driving unit comprises two driving parts, and the two driving parts respectively cooperate with the two sub-wheels. The driving unit is disposed between the two sub-wheels. The driving unit rotates around the rotating shaft to drive the driving part to alternately push the sub-wheels to rotate.

FIG. 2*a* and FIG. 2*b* are schematic diagrams showing the structure of a driving unit 200 including only one driving part 210 according to an embodiment of the present invention. FIG. 2*a* is a schematic view of the structure as viewed in the direction of the arrow of FIG. 2*b*, and FIG. 2*b* is a schematic view of the structure as seen by the direction of the arrow in FIG. 2*a*.

The rotating shaft 270 is disposed on a base (not shown), and the power unit 260 pulls the driving unit 200 to rotate around the rotating shaft 270 to drive the driving part 210 and the positioning part 22 to move. Since the driving unit 200 has only one driving part 210, in the embodiment of the present invention, only one driving wheel 230 is engaged with the driving part 210. And the driving part 210, an elastic member, can not only push the teeth when rotating in one direction, but also slide on the teeth while rotating in the opposite direction. In order to show the structure of the driving unit 200 clearly, the driving wheels are not shown in FIG. 2*b*.

FIG. 3 is a schematic structural diagram of a driving unit 300 including four driving parts 310 according to an embodiment of the present invention.

The driving apparatus of the embodiment of the present invention does not limit the number of driving parts, and there may be one or two, as described above. Further, there may be three, four or more than four driving parts. When there are two or more driving parts, the driving wheel includes two sub-wheels, as shown in FIG. 1, thus different driving parts respectively cooperate with corresponding sub-wheels.

As shown in FIG. 3, in one embodiment of the present invention, the driving unit 300 includes four driving parts 310*a*, 310*b*, 310*c*, and 310*d*. 310*a* and 310*c* are disposed on one side of the driving unit 300 and cooperate with one sub-wheel, while 310*b* and 310*d* are disposed on the other side of the driving unit 300 to cooperate with the other sub-wheel. Obviously, in other embodiments of the present invention, when the number of the driving parts 310 is an odd number greater than or equal to 3, the numbers of driving parts disposed on each side of the driving unit 300 are different, that is, the numbers of driving parts matched with each sub-wheel are different, but the driving requirements of the present invention can still be satisfied.

It should be noted that, in the embodiment of the present invention, the tooth pitch of the gear can be set according to the situation, and when the driving part of one side pushes the gear teeth, the driving part of the other side slides on the surface of the gear tooth, The sliding distance can be less than, or equal to, or greater than one pitch. When the driving unit rotates in the other direction, the position of the previously sliding driving part is adjusted after a period of time, and the gear teeth can also be driven to drive the driving wheel to move, which is not specifically limited.

Embodiments in which the driving unit includes two driving parts will be described in detail below.

FIG. 4*a* to FIG. 4*c* are respectively two top plan views and a side view of the position detecting area 180 and the positioning unit 120 according to an embodiment of the present invention. FIG. 4*a* is a schematic top view of the structure taken along the direction of the arrow of FIG. 4*b* (when the similar viewing angles of the structural diagrams in other embodiments are the same as here, it will not be described below).

As shown in FIG. 4*a* to FIG. 4*c*, in an embodiment of the invention, position detecting area 180 includes a plurality of contactors spaced apart. The contactors are in the shape of a spherical cap and are arranged in a straight line at intervals. As shown in FIG. 4*c*, in another embodiment of the invention, the contactor spacing arrangement is in the form of an arc.

It should be noted that, in other embodiments of the present invention, the shape and arrangement of the contactors may also include other types, which are not specifically limited herein, as long as the conditions for generating the position signals can be satisfied.

In the embodiment shown in FIG. 4*a* to FIG. 4*c*, there is only one positioning part 120 and one position detecting area 180, and the positioning part 120 and the position detecting area 180 are disposed on the same side of the driving unit 100. In other embodiments of the present invention, the positioning part 120 and the position detecting area 180 may be disposed at other positions as long as they can cooperate with each other to satisfy the conditions for detecting position and triggering position signal, and are not specifically limited herein.

FIG. 4*b* is a schematic side view of the structure taken along the direction of the arrow of FIG. 4*a* (when the similar viewing angles of the structural diagrams in other embodiments are the same as here, it will not be described below). When the driving unit 100 is rotated to different positions, the positioning part 120 is in electrical contact with different contactors, and different position signals can be triggered. Specifically, in the embodiment of the present invention, the potentials of the different contactors are different, and the positioning part 120 also has a fixed potential (the potential may be a negative value, 0 or a positive value). Therefore, when the positioning part 120 is in contact with different contactors, the potential of the contactor changes, or the potential difference measured at different positions changes, and the electric signal generated by the change of the potential (or the potential difference) which serves as position signal is transmitted to the control unit through the wire 181. The control unit determines whether the driving unit 100 has reached the end of rotation in the selected movement mode (including the movement mode and/or the movement rate mode). If the required movement mode is not met, that is, the driving unit 100 has not reached the end of rotation in that direction, the control unit continues to instruct the power unit 160 to pull the driving unit 100, leading driving unit 100 to continue rotating in that direction until the end of the rotation is reached. And then it can rotate in the other direction.

Obviously, when the driving unit 100 rotates to a terminal point, it stops rotating until the driving unit 100 performs the next movement instruction.

Specifically, in one embodiment of the invention, the different contactors have different positive potentials and the potential of the positioning part 120 is zero (or ground, or negative). When the positioning part 120 is in contact with different contactors, the control unit can receive different potential signals representing different position signals, based on which the control unit controls the force applied by the power unit 160.

As shown in FIG. 4*a* to FIG. 4*c*, it is obvious that there are multiple contactors in the embodiment of the present invention. According to different actual movement requirements, after receiving the instruction of the selected movement mode, the control unit controls the power unit 160 to ensure that the driving unit 100 stops rotating after contacting a specific contactor, and then starts to rotate in the other direction. By analogy, the driving unit 100 can complete the rotation cycle within a certain width range, thereby completing the movement process of the selected movement mode. Therefore, in an embodiment of the invention, the driving unit 100 rotates over a plurality of optionally different width ranges to provide the driving apparatus with a plurality of different rotational modes.

As shown in FIG. 4*b*, the contactors of the position detecting area 180 are protruding from the surface of the base (not shown) to ensure sufficient contact with the positioning part 120. Each contactor is connected to the control unit via a wire 181 through which an electrical signal can be passed.

FIG. 4*c* is a schematic structural view of a contact of a position detecting area 280 according to another embodiment of the present invention. Multiple contactors spaced apart are arranged in an arc shape, and the radian is coincident with the rotation radian of the positioning part 220. Its side view is identical to FIG. 4*b* and will not be described again here.

FIG. 5*a* and FIG. 5*b* are schematic diagrams showing the structure of a position detecting area 380 and a positioning part 320 according to still another embodiment of the present invention.

In the embodiment of the present invention, the position detecting area 380 includes continuous conductive area, and the positioning part 320 can incessantly contact and slide on the position detecting area 380. As described above, the position detecting area 380 and the positioning part 320 are both disposed on the same side of the driving unit 100.

As shown in FIG. 5*b*, the position detecting area 380 is protruding from the surface of the base to facilitate continuous contact with the positioning part 320.

The position detecting area 380 also includes a connection point a at which the wire 381 is connected to the control unit. The position where the positioning part 320 and the position detecting area 380 are in sliding contact is the contact point b. Since the positioning part 320 continuously contacts and slides on the position detecting area 380, the position of the contact point b changes with the rotation of the driving unit 100, and the length of the range D between the connection point a and the contact point b changes. Therefore, the position signal of the driving unit 100 is determined and triggered by measuring the resistance or potential within a certain range D between the connection point a and the contact point b. During the rotation of the driving unit 100, the width and the range between the contact point b and the connection point a are changing, and the measured resistance or potential is also changing. Different resistance values or potential values correspond to different positions, therefore unique position information can be sent to the control unit through electrical signal. Therefore, the driving unit 100 of the embodiment of the present invention can be rotated within a plurality of different widths ranges under the control of the control unit.

It should be noted that other embodiments of the present invention do not specifically limit the position and the number of the connection point a, and the number of position detecting area 380 and the positioning part 320 may each be set to be two or more. Through the design of a circuit corresponding with the number of connection points a, much more precise positioning can be achieved.

In some other embodiments of the present invention, the position detecting area is a continuous slide rail on which the positioning part can continuously contact and slide. Or a groove is disposed in the position detecting area, and the positioning part cooperates with the groove to continuously contact and slide in the groove to trigger the position signal, which is not specifically limited herein.

FIG. 6*a* to FIG. 6*b* are schematic diagrams showing the structure of two positioning parts and two position detecting areas according to an embodiment of the present invention.

The driving apparatus of the embodiment of the present invention includes two positioning parts 420*a* and 420*b*, and two position detecting areas 480*a* and 480*b* which both include a plurality of spaced apart contactors. The position detecting area 480*a* cooperates with the positioning part 420*a*, and the position detecting area 480*b* cooperates with the positioning part 420*b*, and they are respectively disposed on each side of the driving unit 100. The manners and working principles of the position detecting area 480*a* and the positioning part 420*a*, or the position detecting area 480*b* and the positioning part 420*b* are respectively matched with the foregoing, and are not described herein again.

As shown in FIG. 6*b*, likewise, each of the contact lead wires 481*a* or 481*b* is connected to the control unit. The positioning parts 420*a* and 420*b* can be respectively in contact with different contactors to trigger different position signals. In one embodiment of the invention, the positioning parts 420*a* and 420*b* can be in contact with different contactors at the same time, and the control unit can receive two position signals simultaneously, which can achieve more precise positioning. In another embodiment of the present invention, during the rotation of the positioning parts 420*a* and 420*b*, only one positioning part may be in contact with the contactors to trigger a position signal without the two positioning parts simultaneously contacting different contactors, and no specific limitation is made here.

It should be noted that, in other embodiments of the present invention, the position detecting area 480*a* on one side may be a continuous conductive area, and the position detecting area 480*b* on the other side may be a plurality of contactors spaced apart, or both of the position detecting areas 480*a* and 480*b* may be continuous conductive areas. No specific restrictions are made here.

Moreover, in one embodiment of the present invention, the positioning part includes two parts 420*a* and 420*b*, and there is only one position detecting area. Similarly, the position detecting area includes a plurality of contactors spaced apart or continuous conductive areas. In this case, the range of the position detecting area is wide, and spans from one side of the driving unit 100 to the other side, and can be in contact with the two positioning parts 420*a* and 420*b*, respectively.

FIG. 7*a* to FIG. 7*b* are schematic diagrams showing the structure of a position detecting area 580 and a positioning part 520 for triggering a magnetic signal according to an embodiment of the present invention.

The manner of interaction between the position detecting area 580 and the positioning part 520 also includes a non-contact type.

As in the embodiment of the present invention, the position detecting area 580 includes a plurality of first magnetic sensing points spaced apart, and the positioning part 520 includes a second magnetic sensing point. When the driving unit 100 rotates to different positions, the second magnetic sensing point interacts with different first magnetic sensing points to cause a change in the strength and direction of the magnetic field. At different positions, the strength and direction of the magnetic field will be different, thus triggering different magnetic signals. The magnetic signal is transmitted to the control unit through the connecting line 581, serving as a position signal of the driving unit 100.

Similarly, in other embodiments of the invention, the position detecting area may further comprise a continuous magnetic induction area, or as previously described, the driving apparatus comprises two position detecting areas 580 and two positioning parts 520. The two position detecting areas 580 may include a plurality of first magnetic sensing points spaced apart, or include continuous magnetic induction areas at the same time. Or one of the position detecting areas 580 may include magnetic sensing points spaced apart, while the other position detecting area being a continuous magnetic induction area. Or in the driving apparatus, a wide range of position detecting area 580 and two positioning parts 520 are included, and are not specifically limited herein as long as it can trigger magnetic position signals.

The principle and manner of controlling the rotation of the driving unit 100 according to the triggered magnetic signal are consistent with those described above, and are not described herein again. Different from the previous method of triggering electrical signals, the second magnetic sensing point and the first magnetic sensing point or the continuous magnetic induction area can trigger different magnetic position signals without direct contact. In order not to affect the motion of the driving unit 100, the magnetic field strength of the first magnetic sensing point, the second magnetic sensing point or the continuous magnetic induction area may be small as long as the purpose of generating magnetic signals can be achieved.

In another embodiment of the present invention, the positioning part and the position detecting area are different plates of the capacitor with a certain distance between them. When the position of the positioning part changes, the capacitor plate area can change, thus causing changes in capacitance and triggering different position signals.

It should be noted that, in other embodiments of the present invention, other non-contact methods for triggering position signals are also included, such as the way of mutual inductance, which is not specifically limited herein, as long as the target measurement value can be acquired by the position change of the positioning part.

In the embodiment of the invention illustrated in FIG. 4*a* to FIG. 7*b*, the terminal points of rotation of the driving unit 100 are all controlled by the control unit according to position signals, rather than being stopped by a fixedly configured structure block. It is just because of this above mode of control that the driving apparatus of the embodiments of the present invention has a variety of alternative movement modes or movement rate modes.

FIG. 8 is a block diagram showing the structure of movable position detecting area 680 according to an embodiment of the present invention.

In the embodiment of the present invention, the position detecting area 680 includes two movable conductive retaining walls 680*a* and 680*b*. In this case, the part of the driving unit 100 that can contact the conductive retaining wall is the positioning part 620. The positioning part 620 rotates between the two conductive retaining walls. The control unit is capable of controlling the movement of the conductive retaining wall. Thus, in an embodiment of the invention, the electrically conductive retaining wall 680 can simultaneously trigger a position signal and block the driving unit 100 from rotating.

After the driving unit 100 rotates, it contacts the conductive retaining wall 680*a* or 680*b* through the positioning part 620, thereby triggering the position signal. Electrical signals are transmitted to the control unit via wires 681*a* or 681*b*. When the driving unit 100 is in contact with the conductive retaining wall 680*a*, the rotation terminal point signal is triggered, and the driving unit 100 can start to rotate in the other direction. The rotation range of the driving unit 100 between the conductive retaining walls is $S_1$. When the conductive retaining walls 680*a* and/or 680*b* are moved horizontally, the range of rotation of the driving unit 100 between the conductive barriers is $S_2$, and it is obvious that the width ranges $S_1$ and $S_2$ are different. By analogy, by changing the position of the movable conductive retaining wall, the driving unit 100 can be rotated over a range of different widths, ultimately forming different and optional movement modes.

Obviously, in one embodiment of the present invention, one side of the driving unit 100 is provided with one conductive retaining wall, and the other side can be disposed as a plurality of contactors spaced apart, or continuous conductive areas, or magnetic sensing points, as described above. In this case, the driving unit 100 is correspondingly provided with a positioning part that cooperates with the above contactors, areas or points. It is also possible to trigger different position signals, forming different and optional movement modes.

It should be noted that, in other embodiments of the present invention, the conductive retaining wall can also be vertically moved, or the range of rotation of the driving unit 100 can be adjusted in a manner of oblique movement or three-dimensional space movement. As long as the conditions for triggering different positions signals can be satisfied, there are no specific restrictions herein.

In summary, the driving apparatus disclosed in the embodiment of the present invention has various optional motion ranges under the control of the control unit, and the driving mode can be flexibly controlled to improve driving efficiency.

While the invention has been described in detail with reference to the specific embodiments of the present invention, it should be understood that it will be appreciated by those skilled in the art that the above embodiments may be modified without departing from the scope and spirit of the invention. The scope of the invention is defined by the appended claims.

The invention claimed is:

1. A driving apparatus comprising:

a driving unit, wherein the driving unit includes a driving part and two positioning parts, and the driving unit drives the driving part and the positioning parts to move in different directions;

a position detecting area, wherein the position detecting area comprises two position detecting sub-areas, each of the two position detecting sub-areas includes a plurality of contactors spaced apart, and each of the two positioning parts interacts with a respective one of the two position detecting sub-areas at different positions to trigger different position signals, wherein, along different moving directions of the positioning parts, the plurality of contactors of each of the two position detecting sub-areas includes at least one intermediate contactor positioned between two terminal contactors along a path of a respective one of the positioning parts;

a power unit connected to the driving unit, wherein the power unit applies a force to cause the movement of the driving unit; and a control unit, wherein the control unit is connected to the position detecting area for receiving the position signals, and the control unit is connected to the power unit, and according to the position signals, the control unit controls a direction of the force applied by the power unit, so that the driving unit is movable in multiple different width ranges, and forming different infusion modes, wherein each of the positioning parts, while rotating, is able to be in electrical contact with at least some of the plurality of contactors, wherein the different contactors have different potentials, each of the positioning parts has a fixed potential, and when each of the positioning parts contacts one of the contactors, the potential of the one of the contactors changes and triggers a unique position signal, wherein the control unit determines whether the driving unit reaches an end of rotation in a selected one of the infusion modes, wherein when the selected infusion mode is not met, the driving unit does not reach the end of rotation and the control unit continues to instruct the power unit to pull the driving unit, leading the driving unit to continue rotating until the end of rotation is reached, wherein the position signals determine different rotation terminal points of the driving unit in different rotation cycles, so that the driving unit is able to stop at a plurality of optional positions, thereby defining the multiple different width ranges, wherein the rotation terminal points are all controlled by the control unit according to the position signals, wherein when the selected infusion mode is met, the driving unit stops rotating once it reaches the rotation terminal point corresponding to the selected infusion mode.

2. The driving apparatus of claim 1, wherein the driving apparatus further comprises a driving wheel, a circumferential surface of the driving wheel is provided with gear teeth, the driving unit rotates to drive the driving part and the positioning parts to move, and the driving part pushes the gear teeth to drive the driving wheel to rotate.

3. The driving apparatus of claim 2, wherein the driving wheel comprises two sub-wheels spaced apart, the driving unit is arranged between the two sub-wheels, the driving unit comprises a second driving part, and the two driving parts respectively cooperate with the two sub-wheels.

4. The driving apparatus of claim 3, wherein the driving unit includes at least a third driving part, each driving part of the at least three driving parts cooperating with a corresponding one of the sub-wheels.

5. The driving apparatus of claim 4, wherein the at least a third driving part comprises a third driving part and a fourth driving part, and two of the four driving parts are disposed on each side of the driving unit and cooperate with the corresponding sub-wheels.

6. The driving apparatus of claim 1, wherein each of the positioning parts of the driving unit interacts with the respective one of the position detecting sub-areas at different positions in contact or non-contact manners.

7. A drug infusion device, comprising:

a drug storage unit, wherein a piston is disposed in the drug storage unit, a driving rod is connected to the piston, and the driving rod is able to push the piston to move;

a driving unit, wherein the driving unit comprises a driving part and two positioning parts, the driving part drives the driving rod to move, and the driving unit drives the driving part and the positioning parts to move in different directions;

a position detecting area, wherein the position detecting area comprises two position detecting sub-areas, each of the two position detecting sub-areas includes a plurality of contactors spaced apart, and each of the positioning parts interacts with a respective one of the position detecting sub-areas at different positions to trigger different position signals, wherein, along different moving directions of the positioning parts, the plurality of contactors of each of the two position detecting sub-areas includes at least one intermediate contactor positioned between two terminal contactors along a path of a respective one of the positioning parts;

a power unit connected to the driving unit, wherein the power unit applies a force to move the driving unit; and a control unit, wherein the control unit is connected to the position detecting area to receive the position signals, and the control unit is connected to the power unit, according to the position signals, the control unit controls a direction of the force applied by the power unit to move the driving unit in multiple different width ranges to form different and optional infusion modes, wherein each of the positioning parts, while rotating, is able to be in electrical contact with at least some of the plurality of contactors, wherein the different contactors have different potentials, each of the positioning parts has a fixed potential, and when each of the positioning parts contacts one of the contactors, the potential of the one of the contactors changes and triggers a unique position signal, wherein the control unit determines whether the driving unit reaches an end of rotation in a selected one of the infusion modes, wherein when the selected infusion mode is not met, the driving unit does not reach the end of rotation and the control unit continues to instruct the power unit to pull the driving unit, leading the driving unit to continue rotating until the end of rotation is reached, wherein the position signals determine different rotation terminal points of the driving unit in different rotation cycles, so that the driving unit is able to stop at a plurality of optional positions, thereby defining the multiple different width ranges, wherein the rotation terminal points are all controlled by the control unit according to the position signals, wherein when the selected infusion mode is met, the driving unit stops rotating once it reaches the rotation terminal point corresponding to the selected infusion mode.

8. The drug infusion device of claim 7, wherein the driving apparatus further comprises a driving wheel, a circumferential surface of the driving wheel is provided with gear teeth, and the driving unit rotates to drive the driving part and the positioning parts to rotate, the driving part pushes the gear teeth to drive the driving wheel to rotate, and the driving rod is a threaded rod in order to be driven by the driving wheel through a thread.

9. The drug infusion device of claim 8, wherein the driving wheel comprises two sub-wheels spaced apart, the driving unit is arranged between the two sub-wheels, the driving unit comprises a second driving part, and the two driving parts respectively cooperate with the two sub-wheels.

10. The drug infusion device of claim 9, wherein the driving unit includes at least a third driving part, each driving part of the at least three driving parts cooperating with a corresponding one of the sub-wheels.

11. The drug infusion device of claim 10, wherein the at least a third driving part comprises a third driving part and a fourth driving part, and two of the four driving parts are disposed on each side of the driving unit and cooperate with the corresponding sub-wheels.

12. The drug infusion device of claim 7, wherein each of the positioning parts of the driving unit interacts with the respective one of the position detecting sub-areas at different positions in contact or non-contact manners.

* * * * *